(12) United States Patent
Choudhary et al.

(10) Patent No.: US 9,447,057 B2
(45) Date of Patent: Sep. 20, 2016

(54) SCHIFF BASES OF THIAZOLES: A NEW CLASS OF UREASES INHIBITORS

(71) Applicants: Muhammad Iqbal Choudhary, Karachi (PK); Ajmal Khan, Karachi (PK); Khalid M. Khan, Karachi (PK); Nida Ambreen, Karachi (PK); Atia-tul Wahab, Karachi (PK); Atta-ur Rahman, Karachi (PK)

(72) Inventors: Muhammad Iqbal Choudhary, Karachi (PK); Ajmal Khan, Karachi (PK); Khalid M. Khan, Karachi (PK); Nida Ambreen, Karachi (PK); Atia-tul Wahab, Karachi (PK); Atta-ur Rahman, Karachi (PK)

( * ) Notice: Subject to any disclaimer, the term of this patent is extended or adjusted under 35 U.S.C. 154(b) by 0 days.

(21) Appl. No.: 14/310,738

(22) Filed: Jun. 20, 2014

(65) Prior Publication Data

US 2015/0368214 A1    Dec. 24, 2015

(51) Int. Cl.
*A61K 31/40* (2006.01)
*A61K 31/44* (2006.01)
*C07D 277/42* (2006.01)
*C07D 417/12* (2006.01)
*C07D 401/12* (2006.01)
*A61K 31/427* (2006.01)
*A61K 31/4439* (2006.01)

(52) U.S. Cl.
CPC ........... *C07D 277/42* (2013.01); *A61K 31/427* (2013.01); *A61K 31/4439* (2013.01); *C07D 401/12* (2013.01); *C07D 417/12* (2013.01)

(58) Field of Classification Search
CPC . A61K 31/404; A61K 31/4025; A61K 31/40
USPC ......................... 514/414, 422, 426, 427, 342
See application file for complete search history.

(56) References Cited

PUBLICATIONS

Kahn et al. "Schiff Bases of thiazole as antibacterial and antifungal agents," Journal of Pharmacy Research, 2012 vol. 5, No. 1, pp. 651-656.*

* cited by examiner

*Primary Examiner* — Shengjun Wang
(74) *Attorney, Agent, or Firm* — Sarfaraz K. Niazi

(57) ABSTRACT

One embodiment of the invention relates to treating diseases associated with increased urease enzyme activity comprising administering an effective amount of a compound selected from a group consisting of 28 thiazoles Schiff bases. Kinetic studies were performed on ten (10) of the most active compounds.

3 Claims, 6 Drawing Sheets

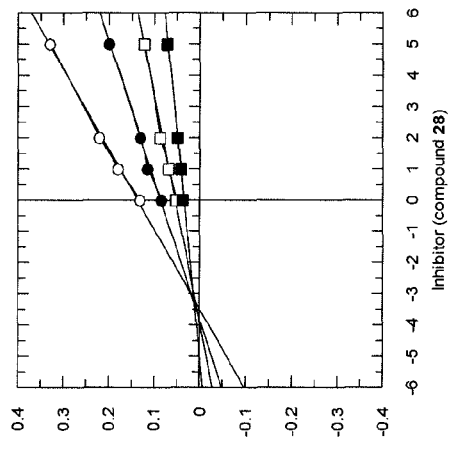
FIG. 1A  FIG. 1B  FIG. 1C
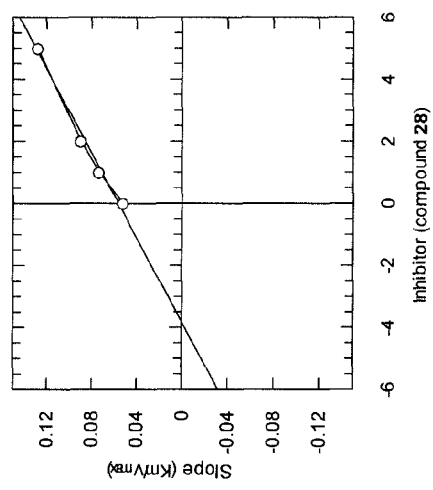
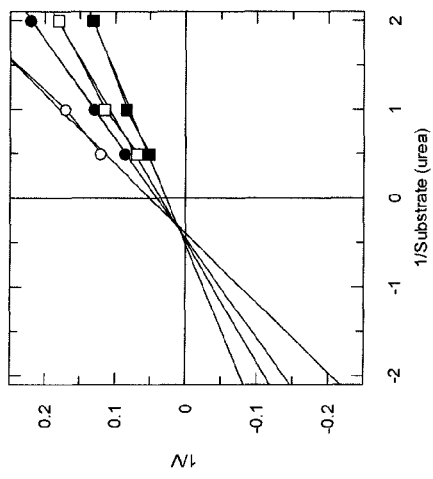
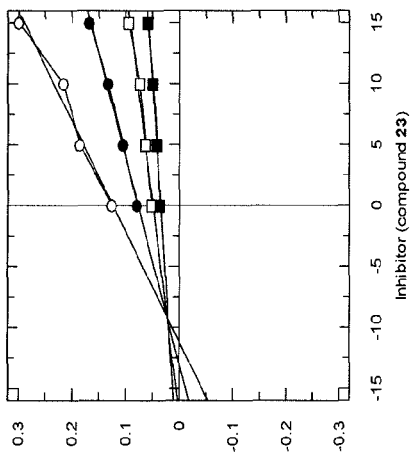
FIG. 2A  FIG. 2B  FIG. 2C
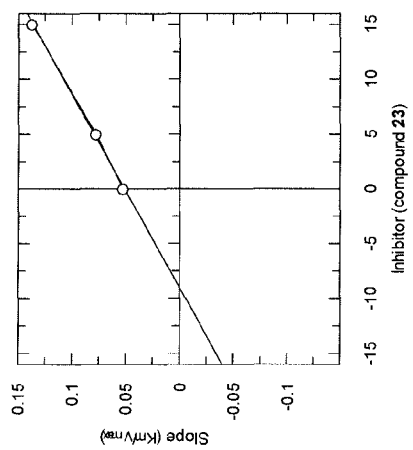
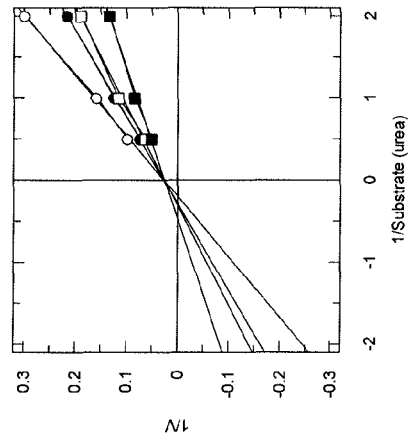

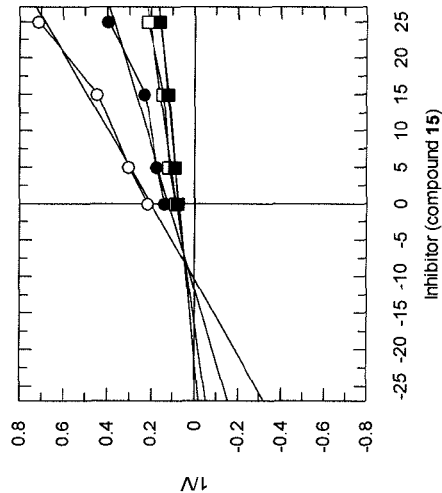
FIG. 3A  FIG. 3B  FIG. 3C
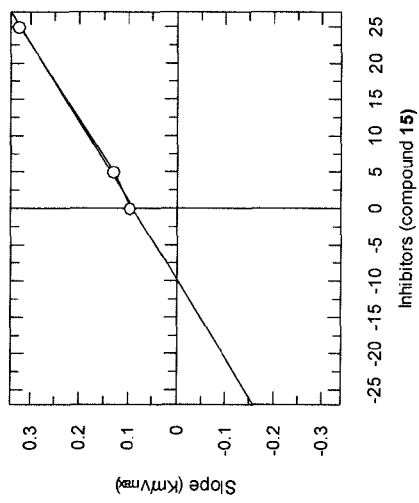
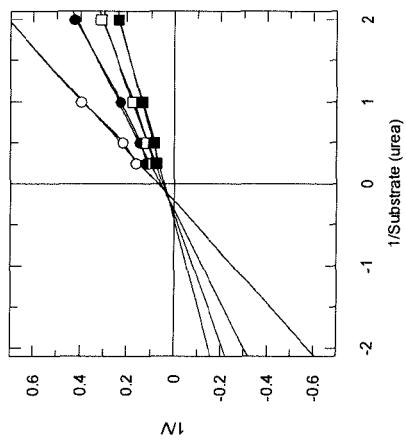
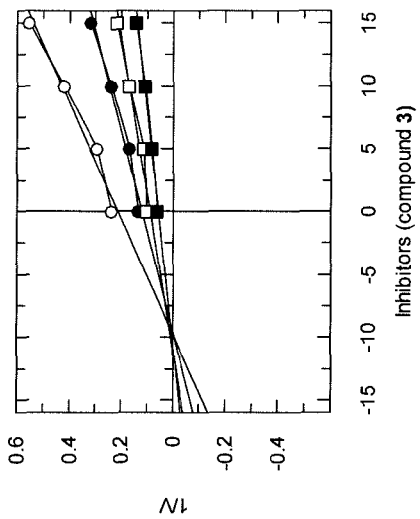
FIG. 4A  FIG. 4B  FIG. 4C
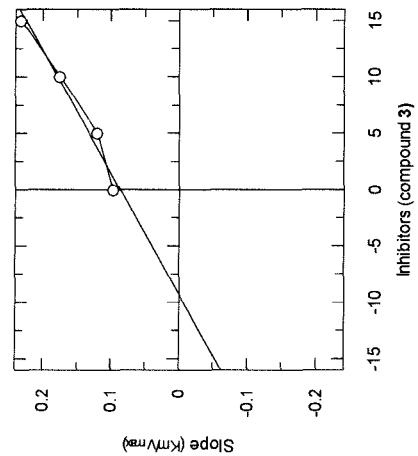
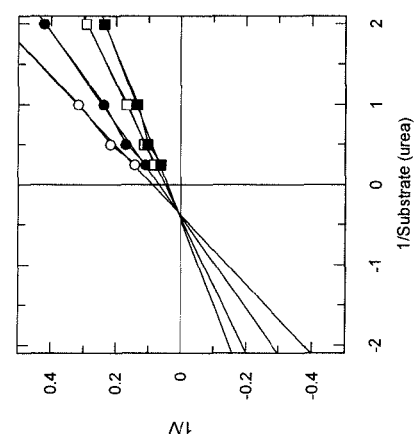

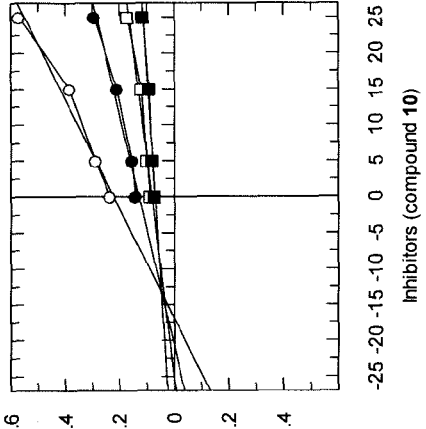
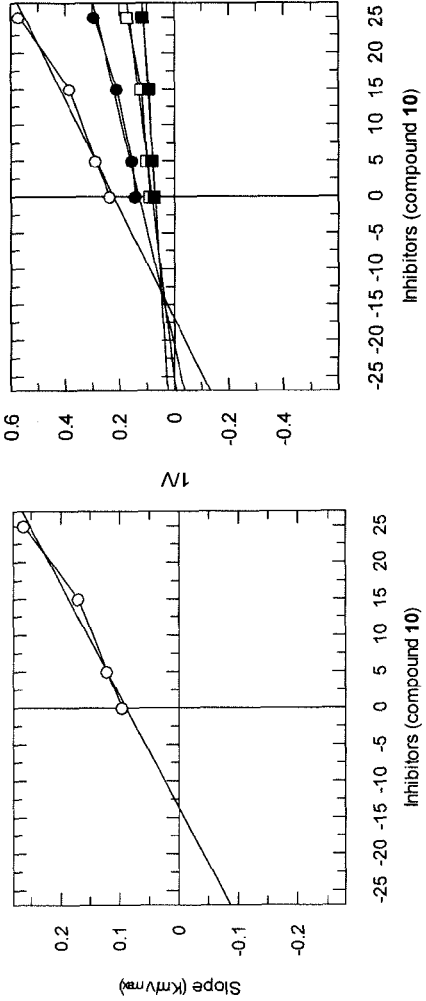
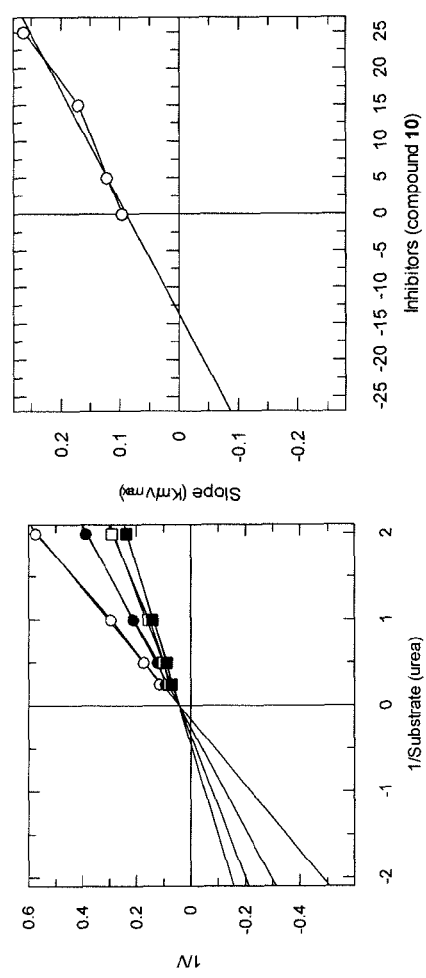
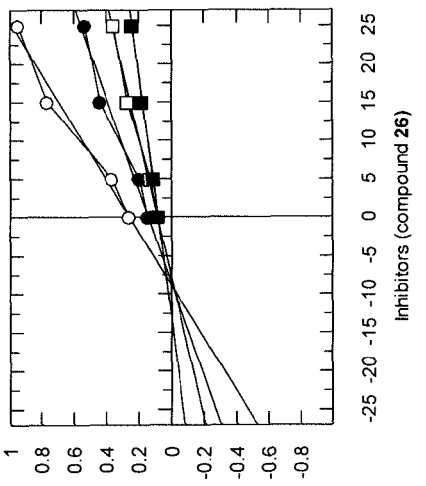
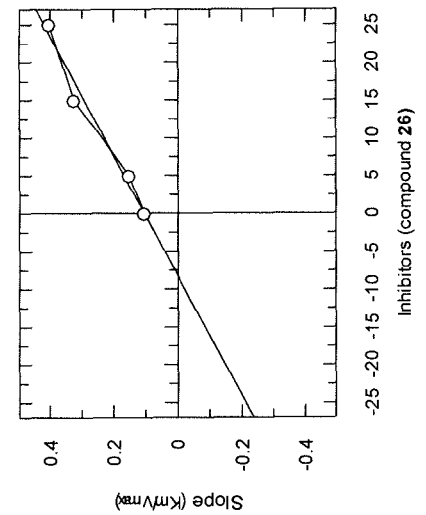
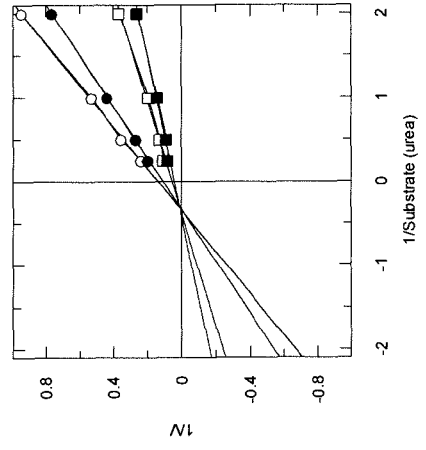
FIG. 5A  FIG. 5B  FIG. 5C
FIG. 6A  FIG. 6B  FIG. 6C

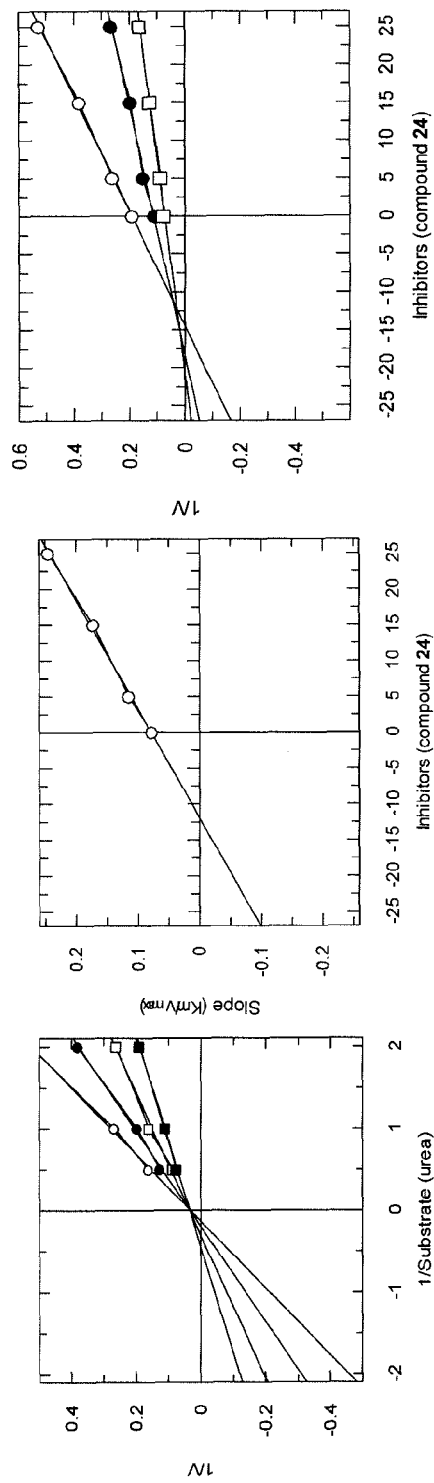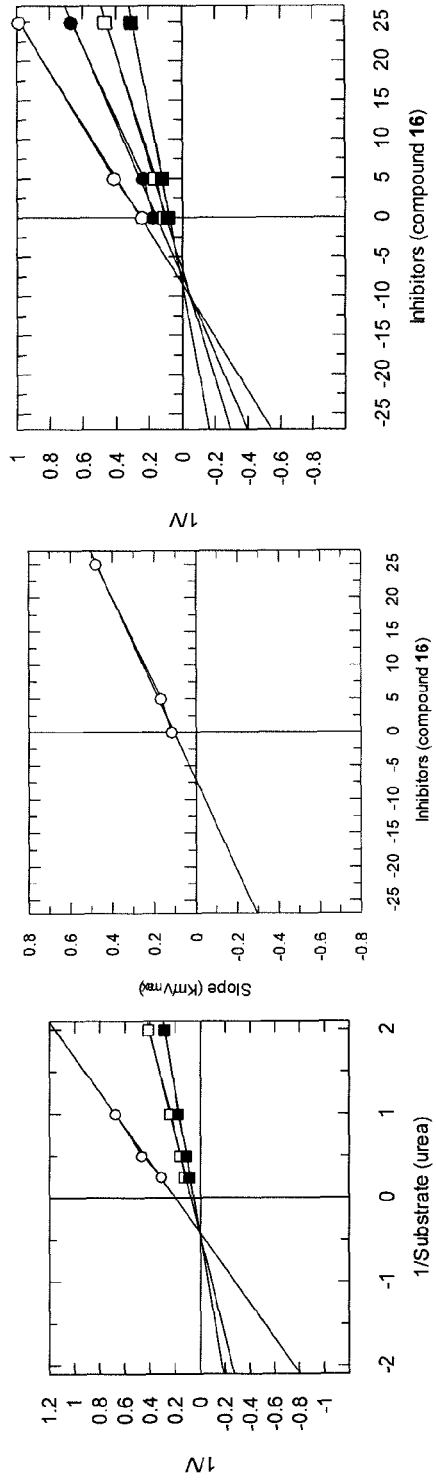

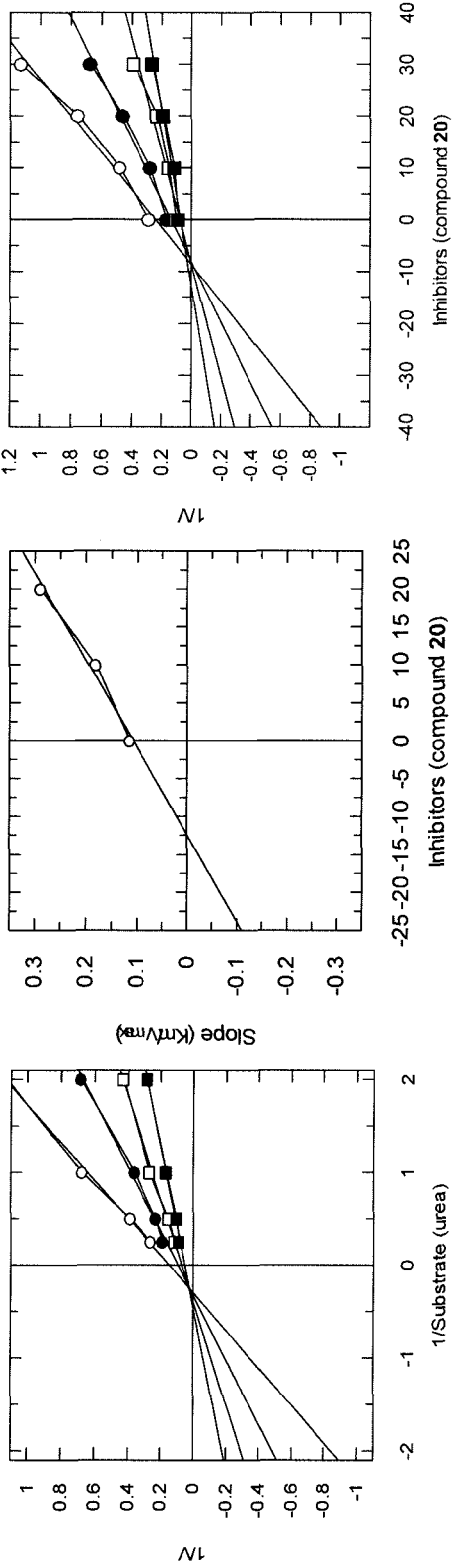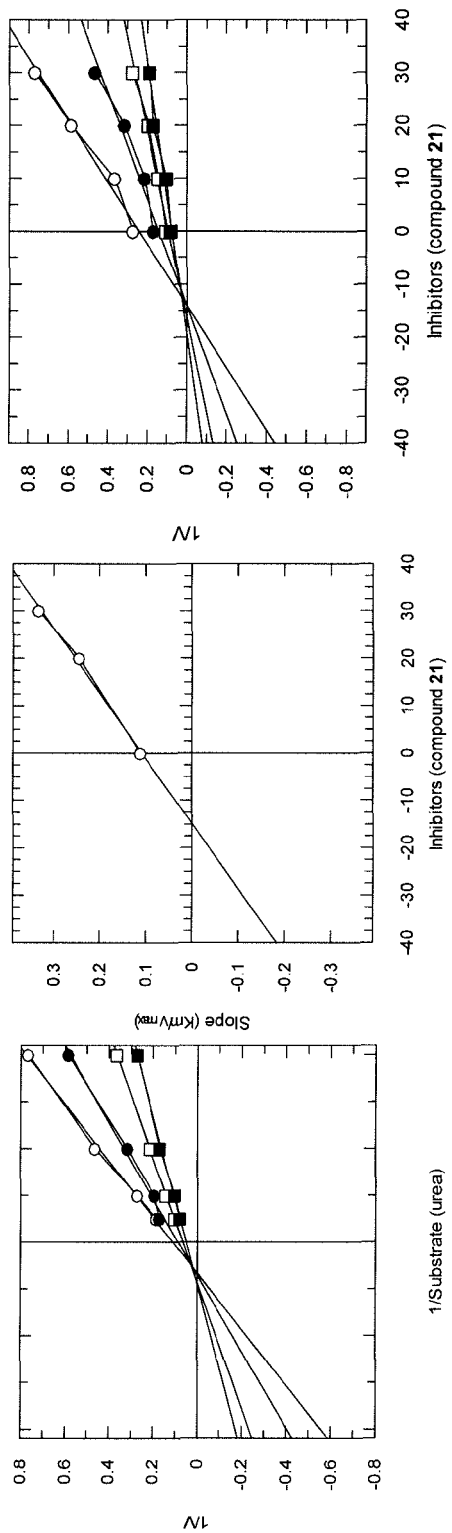
FIG. 9A  FIG. 9B  FIG. 9C
FIG. 10A  FIG. 10B  FIG. 10C

SCHIFF BASES OF THIAZOLES: A NEW CLASS OF UREASES INHIBITORS

BACKGROUND OF THE INVENTION

Urease (urea amidohydrolase EC 3.3.1.5) catalyzes the hydrolysis of urea to form ammonia and carbamate. The later compound spontaneously hydrolyzes at physiological pH to form carbonic acid and a second molecule of ammonia.

Urea is a major nitrogenous waste product of biological actions which is rapidly metabolized by microbial activities. The enzyme is widely distributed in a variety of bacteria, fungi and plants, thus playing an important role in the circulation of nitrogen in nature as they catalyzes the urea degradation to supply these organisms with a source of nitrogen for growth.

In agriculture, high urease activity causes significant environmental and economic problems by releasing abnormally large amounts of ammonia into the atmosphere during urea fertilization (the most widely used fertilizer in the world). This further induces plant damage primarily by depriving plants from their essential nutrients and secondly through ammonia toxicity and carbon dioxide release that increases the pH of the soil. Many microorganisms use this enzyme to provide a source of nitrogen for growth, as it plays an important role in plant nitrogen metabolism during the germination process. The presence of urease activity in soils is exploited in the widespread agricultural practices for enhancing crop yields.

Urease belongs to a family of highly conserved urea-hydrolyzing enzymes. Urease is known to be one of the major causes of pathologies induced by *Helicobacter pylori*, thus allow them to survive at low pH of the stomach and, therefore, play an important role in the pathogenesis of gastric and peptic ulcer. *Proteus mirabilis* and *Yersinia enterocolitica* are responsible for urolithiasis and involve in the development of acute pyelonephritis and infection-induced reactive arthritis, respectively. The obvious remedy for treating bacterial infection with antimicrobials has often proven futile, and only a few combination regiments have reached clinical practice. Thus the need for alternative or novel treatment is evident.

The discovery of potent and safe urease inhibitors have been a very important area of pharmaceutical research due to the involvement of ureases in different pathological conditions.

Thiazole derivatives have attracted major interest of bio-organic chemists due to their antimicrobial and other biological activities. They exhibit prominent antiviral, anti-mycobacterial and anti-proliferative activities. Thiazole derivatives have been found to have analgesic, anti-inflammatory, anti-nociceptive, and selective acetyl CoA carboxylase-2 inhibitory activity.

BRIEF SUMMARY OF THE INVENTION

Urease, a nickel-dependent metalloenzyme, is synthesized by plants, bacteria, and fungi. It catalyzes the hydrolysis of urea into ammonia and carbon dioxide. Various diseases are associated with the hyperactivity of ureases. For example, the role of urease in the development of kidney stones, pyelonephritis and peptic ulcers are well understood. Urease inhibitors, therefore, have attracted much attention as potent anti-ulcer drugs. Urease also has a significant role in plant nitrogen metabolism. Excessive levels of soil urease can degrade urea fertilizer too rapidly and result in phytopathic effects leading to the loss of volatile ammonia. In the present invention, we discovered a novel class of urease inhibitors, Schiff bases of thiazoles, by using high through-put screening methods (Table-1).

One embodiment of the invention is a method of treating diseases associated with urease enzyme comprising administering to a mammal, preferably a human, in need thereof an effective amount of a compound of the formula shown below wherein R is selected from a group consisting of 28 thiazoles Schiff bases shown in Table 1. In order to describe their mode of inhibition the kinetics studies of ten most active compounds were also performed.

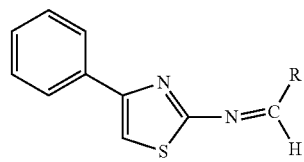

TABLE 1

Urease inhibitory activities of thiazole Schiff bases Compounds 1-28.

| Compound No. | R | $IC_{50} \pm SEM^{a}$ (μM) |
|---|---|---|
| 1 | N-[5a,10c-Dihydro-1-pyrenylmethylidene]-N-(4-phenyl-1,3-thiazol-2-yl)amine | 2.80 ± 0.07 |
| 2 | N-[1H-indol-3-yl-methylidene]-N-(4-phenyl-1,3-thiazol-2-yl)amine | 8.56 ± 0.027 |
| 3 | 2-Ethoxy-6-{[(4-phenyl-1,3-thiazol-2-yl)imino]methyl}phenol | 7.90 ± 0.08 |
| 4 | N-[4-Ethoxyphenyl)methyl-idene]-N-(4-phenyl-1,3-thiazol-2-yl)amine | 11.16 ± 0.02 |

TABLE 1-continued

Urease inhibitory activities of thiazole Schiff bases Compounds 1-28.

| Compound No. | R | $IC_{50} \pm SEM^a$ (μM) |
|---|---|---|
| 5 | N-(4-Phenyl-1,3-thiazol-2-yl)-N-[4-pyridinylmethyl-idene]amine | 7.60 ± 0.08 |
| 6 | 2-Methoxy-6-{[(4-phenyl-1,3-thiazol-2-yl)imino]methyl}phenol | 8.80 ± 0.04 |
| 7 | N-[2-Naphthylmethyl-idene]-N-(4-phenyl-1,3-thiazol-2-yl)amine | 9.33 ± 0.02 |
| 8 | 4-Chloro-2-{[(4-phenyl-1,3-thiazol-2-yl)imino]methyl}phenol | 8.13 ± 0.02 |
| 9 | N-[4-Isopropylphenyl)methylidene]-N-(4-phenyl-1,3-thiazol-2-yl)amine | 14.5 ± 0.16 |
| 10 | N-[(5-Methyl-2-furyl)methylidene]-N-(4-phenyl-1,3-thiazol-2-yl)amine | 17.83 ± 0.07 |
| 11 | N-[4-Nitrophenyl)methyl-idene]-N-(4-phenyl-1,3-thiazol-2-yl)amine | 32.5 ± 0.02 |
| 12 | 4-{[(4-Phenyl-1,3-thiazol-2-yl)imino]methyl}phenol | 20.16 ± 0.07 |
| 13 | N-[4-Methoxyphenyl)methylidene]-N-(4-phenyl-1,3-thiazol-2-yl)amine | 22.33 ± 0.05 |
| 14 | N-[4-(Dimethylamino)phenyl]methylidene}-N-(4-phenyl-1,3-thiazol-2-yl)amine | 20.36 ± 0.11 |
|  | Thiourea$^b$ | 21.0 ± 0.11 |
| 15 | CH—CH$_2$—CH$_3$<br>N-(4-phenyl-1,3-thiazol-2-yl)-N-[Propylidene]amine | 20.43 ± 0.07 |
| 16 | 2-{[(4-Phenyl-1,3-thiazol-2-yl)imino]methyl}phenol | 12.43 ± 0.14 |
| 17 | 1-(2-Methoxyphenyl)-2-[(4-phenyl-1,3-thiazol-2-yl)imino]-1-ethanone | 36.66 ± 0.12 |
| 18 | N-[4-(Methylsulfanyl)phenyl]methylidene}-N-(4-phenyl-1,3-thiazol-2-yl)amine | 6.96 ± 0.05 |
| 19 | N-[Phenylmethyl-idene]-N-(4-phenyl-1,3-thiazol-2-yl)amine | 16.76 ± 0.05 |

TABLE 1-continued

Urease inhibitory activities of thiazole Schiff bases Compounds 1-28.

| Compound No. | R | IC$_{50}$ ± SEM$^a$ (μM) |
|---|---|---|
| 20 | N-[2-Chlorophenyl)methylidene]-N-(4-phenyl-1,3-thiazol-2-yl)amine | 13.03 ± 0.02 |
| 21 | N-[1-Naphthylmethylidene]-N-(4-phenyl-1,3-thiazol-2-yl)amine | 23.06 ± 0.11 |
| 22 | N-[2-Fluorophenyl)methylidene]-N-(4-phenyl-1,3-thiazol-2-yl)amine | 17.93 ± 0.07 |
| 23 | 3-{[(4-Phenyl-1,3-thiazol-2-yl)imino]methyl}-1,2-benzenediol | 19.63 ± 0.19 |
| 24 | N-[3,4-Dimethoxyphenyl)methylidene]-N-(4-phenyl-1,3-thiazol-2-yl)amine | 11.3 ± 0.08 |
| 25 | N-[2,6-Dichlorophenyl)methylidene]-N-(4-phenyl-1,3-thiazol-2-yl)amine | 22.33 ± 0.11 |
| 26 | N-[4-Chlorophenyl)methylidene]-N-(4-phenyl-1,3-thiazol-2-yl)amine | 19.0 ± 0.04 |
| 27 | 4-Phenyl-N-[(2,3,4-trimethoxyphenyl)methylidene]-1,3-thiazol-2-amine | 24.56 ± 0.02 |
| 28 | N-[3-Nitrophenyl)methylidene]-N-(4-phenyl-1,3-thiazol-2-yl)amine | 10.50 ± 0.04 |

BRIEF DESCRIPTION OF THE DRAWING

FIG. 1A depicts the inhibition of urease by compound 1 and is the Lineweaver-Burk plot of reciprocal of rate of reaction (velocities) versus reciprocal of substrate (urea) in absence (■), and in presence of 1 μM (□), 2 μM (•), and 5 μM (○) of compound 1.

FIG. 1B is the secondary replot of Lineweaver-Burk plot between the slopes of each line on Lineweaver-Burk plot versus different concentrations of compound 1.

FIG. 1C is the Dixon plot of reciprocal of rate of reaction (velocities) versus different concentrations of compound 1.

FIG. 2A depicts the inhibition of urease by compound 2 and is the Lineweaver-Burk plot of reciprocal of rate of reaction (velocities) versus reciprocal of substrate (urea) in absence (■), and in presence of 5 μM (□), 10 μM (•), and 15 μM (○) of compound 2.

FIG. 2B depicts the secondary replot of Lineweaver-Burk plot between the slopes of each line on Lineweaver-Burk plot versus different concentrations of compound 2.

FIG. 2C depicts the Dixon plot of reciprocal of rate of reaction (velocities) versus different concentrations of compound 2.

FIG. 3A depicts the inhibition of urease by compound 3 and is the Lineweaver-Burk plot of reciprocal of rate of reaction (velocities) versus reciprocal of substrate (urea) in absence (■), and in presence of 5 μM (□), 15 μM (•), and 25 μM (○) of compound 3.

FIG. 3B depicts the secondary replot of Lineweaver-Burk plot between the slopes of each line on Lineweaver-Burk plot versus different concentrations of compound 3.

FIG. 3C depicts the Dixon plot of reciprocal of rate of reaction (velocities) versus different concentrations of compound 3.

FIG. 4A depicts the inhibition of urease by compound 4 and is the Lineweaver-Burk plot of reciprocal of rate of reaction (velocities) versus reciprocal of substrate (urea) in absence (■), and in presence of 5 μM (□), 10 μM (•), and 15 μM (○) of compound 4.

FIG. 4B depicts the secondary replot of Lineweaver-Burk plot between the slopes of each line on Lineweaver-Burk plot versus different concentrations of compound 4.

FIG. 4C depicts the Dixon plot of reciprocal of rate of reaction (velocities) versus different concentrations of compound 4.

FIG. 5A depicts the inhibition of urease by compound 5 and is the Lineweaver-Burk plot of reciprocal of rate of reaction (velocities) versus reciprocal of substrate (urea) in absence (■), and in presence of 5 μM (□), 15 μM (•), and 25 μM (○) of compound 5.

FIG. 5B depicts the secondary replot of Lineweaver-Burk plot between the slopes of each line on Lineweaver-Burk plot versus different concentrations of compound 5.

FIG. 5C depicts the Dixon plot of reciprocal of rate of reaction (velocities) versus different concentrations of compound 5.

FIG. 6A depicts the inhibition of urease by compound 6 and is the Lineweaver-Burk plot of reciprocal of rate of reaction (velocities) versus reciprocal of substrate (urea) in absence (■), and in presence of 5 μM (□), 15 μM (•), and 25 μM (○) of compound 6.

FIG. 6B depicts the secondary replot of Lineweaver-Burk plot between the slopes of each line on Lineweaver-Burk plot versus different concentrations of compound 6.

FIG. 6C depicts the Dixon plot of reciprocal of rate of reaction (velocities) versus different concentrations of compound 6.

FIG. 7A depicts the inhibition of urease by compound 7 and is the Lineweaver-Burk plot of reciprocal of rate of reaction (velocities) versus reciprocal of substrate (urea) in absence (■), and in presence of 5 μM (□), 15 μM (•), and 25 μM (○) of compound 7.

FIG. 7B depicts the secondary replot of Lineweaver-Burk plot between the slopes of each line on Lineweaver-Burk plot versus different concentrations of compound 7.

FIG. 7C depicts the Dixon plot of reciprocal of rate of reaction (velocities) versus different concentrations of compound 7.

FIG. 8A depicts the inhibition of urease by compound 8 and is the Lineweaver-Burk plot of reciprocal of rate of reaction (velocities) versus reciprocal of substrate (urea) in absence (■), and in presence of 5 μM (□), 15 μM (•), and 25 mM (•) of compound 8.

FIG. 8B depicts the secondary replot of Lineweaver-Burk plot between the slopes of each line on Lineweaver-Burk plot versus different concentrations of compound 8.

FIG. 8C depicts the Dixon plot of reciprocal of rate of reaction (velocities) versus different concentrations of compound 8.

FIG. 9A depicts the inhibition of urease by compound 9 and is the Lineweaver-Burk plot of reciprocal of rate of reaction (velocities) versus reciprocal of substrate (urea) in absence (■), and in presence of 5 μM (□), 15 μM (•), and 25 μM (○) of compound 9.

FIG. 9B depicts the secondary replot of Lineweaver-Burk plot between the slopes of each line on Lineweaver-Burk plot versus different concentrations of compound 9.

FIG. 9C depicts the Dixon plot of reciprocal of rate of reaction (velocities) versus different concentrations of compound 9.

FIG. 10A depicts the inhibition of urease by compound 10 and is the Lineweaver-Burk plot of reciprocal of rate of reaction (velocities) versus reciprocal of substrate (urea) in absence (■), and in presence of 10 μM (□), 20 μM (•), and 30 μM (○) of compound 10.

FIG. 10B depicts the secondary replot of Lineweaver-Burk plot between the slopes of each line on Lineweaver-Burk plot versus different concentrations of compound 10.

FIG. 10C depicts the Dixon plot of reciprocal of rate of reaction (velocities) versus different concentrations of compound 10.

DETAILED DESCRIPTION OF THE INVENTION

Figure 11:
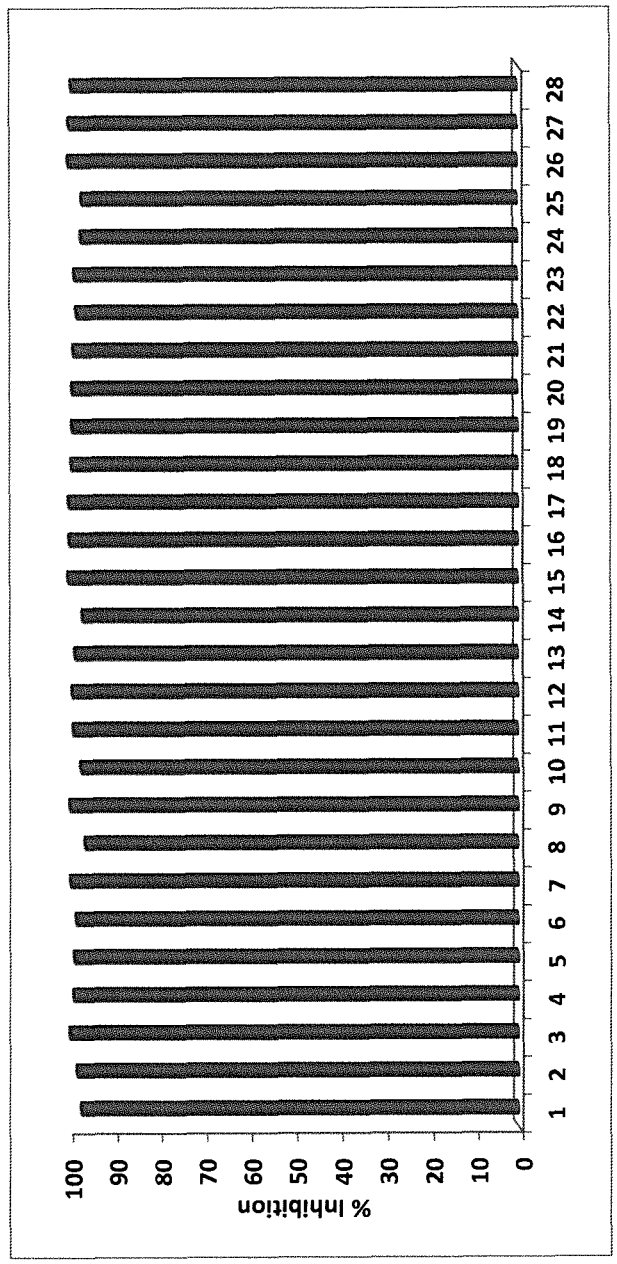
FIG. 11 depicts the percentage inhibition of compounds 1-28 at 0.2 mM concentration.

The Schiff bases of thiazoles were evaluated for their urease inhibitory potential by using the following protocol:

Reaction mixtures consisting of 25 μL (1 unit/well) of Jack bean (*Canavalia ensiformis*) urease, 55 μL of buffer at pH 6.8, 100 mM of urea, and 5 μL of various concentrations of test compounds were incubated at 30° C. for 15 min in 96-well plates. Subsequently 45 μL phenol reagents (1% w/v phenol and 0.005% w/v sodium nitroprussside), and 70 μL of alkali reagent (0.5% w/v NaOH and 0.1% w/v NaOCl) were added to each well. Urease activity through indophenols method was confirmed by the production of ammonia, as described by Weatherburn [12]. After 50 min, the increasing absorbance at 630 nm was measured in a microplate reader SpectraMax M2 (Molecular Devices, CA, USA). All reactions were performed in triplicate in a final volume of 200 μL. Thiourea was used as the standard inhibitor of urease [13]. Finally the results were processed by software SoftMax Pro (Molecular Devices, CA, USA), MS-Excel and Ez-fit. The Percent inhibition was calculated from the formula given below:

$$100-(OD\ of\ test\ compound/OD\ of\ control) \times 100$$

The concentrations of test compounds that inhibited the hydrolysis of substrates by 50% ($IC_{50}$) were determined by monitoring the effect of increasing concentrations of these compounds in the assays on the inhibition values. The $IC_{50}$ values were then calculated using the EZ-Fit Enzyme Kinetics program (Perrella Scientific Inc., Amherst, U.S.A.).

The Lineweaver-Burk plot was used to determine the type of inhibition, while Dixon plot and secondary replete were used for the determination of dissociation constants (Ki). The Ki, $K_m$, and $V_{max}$ were determined by non-linear regression equation. The Ki value was determined from lineweaver-Burk plot. For the calculation of Ki values, initially the $1/V_{maxapp}$ values were determine on y-axis of lineweaver-Burk plot at each junction point of lines of every inhibitor concentration. Secondly the slope of the inhibitor at concentration of each line were determined on Lineweaver-Burk plot and re-plotted against the inhibitor concentrations.

Graphs were plotted using GraFit program. Values of the correlation coefficients, slopes, intercepts, and their standard errors were obtained by the linear regression analysis using the same program. Each point in the constructed graphs represents the mean of the three experiments.

We have synthesized thiazole (4-phenyl-1,3-thaizol-2-amine) Schiff bases 1-28 and evaluated their urease inhibitory potential, according to literature protocol. Previously we have reported the urease inhibitory activity of thiozoles class. For the first time we are going to report the urease inhibitory activity of schiff bases of thiazole. The results demonstrate that the synthesized compounds exhibit excellent inhibitory potential against urease with $IC_{50}$ values in the range of 2.80±0.07-36.66±0.12 µM, in comparison to standard thiourea ($IC_{50}$=21.0±0.011 µM). Compounds 1-10, 12, 14-16, 18-20, 22-24 26, and 28 (Table 1) having $IC_{50}$ values in the range of 2.80±0.07-20.43±0.07 showed excellent urease inhibitory activities, superior than the standard, thiourea ($IC_{50}$=21.4±0.11 µM).

Compounds 11, 13, 17, 21, 25, and 27 (Table 1) demonstrated significant urease inhibitory activity, comparable to standard. Thus compounds 1-10, 12, 14-16, 18-20, 22-24 26, and 28 are lead molecules for further studies as potential anti-urease agents.

Limited SAR study proposes that the activity of compounds mainly due to the sulfur moiety of thiazole ring and nitrogen of Schiff base which may be interact with the Ni of active site of urease. The substitution on aromatic ring may increase or decrease the activity. Compound 1 ($IC_{50}$=2.80±0.07 µM) pyrene ring showed the highest urease inhibitory activity. This may due to interaction of π-bonds of azomethine and pyrene ring with the bi-nickel containing urease active site. However, compound 21 ($IC_{50}$=23.06±0.11 µM) with two fused benzene rings (1-naphthalene) exhibited an inhibitory potential, 8 times less than compound 1. Compound 7 ($IC_{50}$=9.33±0.02 µM) with a 2-naphthalene residue showed activity greater than compound 21, but less than compound 1. Difference in activities of compounds 21 and 7 may be due to the change in position of fused benzene rings (naphthalene) which may create hindrance in π-bonds of azomethine and naphthalene rings with the bi-nickel containing urease enzyme. Compound 18 ($IC_{50}$=6.96±0.054 µM) with methylated sulfur substitution on the para position of phenyl ring showed an excellent inhibition potential which may be due to combined π-bonds interaction of azomethine, phenyl ring, and chelation of sulfur with the bi-nickels. Compound 9 ($IC_{50}$=14.5±0.16 µM), which contains p-isopropyl substituted phenyl residue, showed significant inhibitory potential which may be due to the presence of phenyl ring, azomethine and position of substituent which helps the molecule to chelate with the bi-nickels. Contrary, compound 14 with a closely related structure to compound 9 showed a less activity with an $IC_{50}$ value 20.36±0.11 µM. This activity difference is apparently due to presence of tertiary nitrogen atom in compound 14, instead of an isopropyl group. Compound 26 with a para-substituted chlorine on phenyl ring showed excellent activity ($IC_{50}$=19.0±0.04 µM), whereas compounds 20, 8, and 25 with chloro substituent at different positions of ring showed varying degree of activity with $IC_{50}$ values 13.03±0.02, 8.13±0.02, 22.33±0.11 µM, respectively. This variation in activity may be due to change in position of chloro group, while the compound 8 have hydroxyl group as well, which increase the activity of this compound.

Compounds with alkoxy substitution on phenyl ring (3, 4, 6, 13, 17, 24, and 27) showed $IC_{50}$ values 11.16±0.02, 22.33±0.05, 36.66±0.12, 7.90±0.08, 11.3±0.08, 24.56±0.02, and 7.90±0.08 µM, respectively. The difference in activities may be due to alkoxy groups and other substituent at phenyl residue along with their chelating capacity with Ni atoms of enzyme. When effect of hydroxyl substituted phenyl ring was studied, compounds 12 ($IC_{50}$=20.16±0.07 µM), 16 ($IC_{50}$=12.43±0.14 µM), and 23 ($IC_{50}$=19.63±0.19 µM), with hydroxyl substitution on phenyl ring at ortho position showed notable activity. This can also be seen from the excellent activities of compounds 3, 6, and 8 which are due to combined effect of ortho hydroxyl and other substituents. The effect of ortho hydroxyl substituent is supported by the less activity of unsubstituted compound 19 ($IC_{50}$=16.76±0.054 µM).

Compound 5 ($IC_{50}$=7.60±0.08 µM) is the third most active compound of the series which contains a pyridyl group, instead of a phenyl residue, suggesting that pyridyl moiety along with other structural features is more suitable for binding with the nickel atoms of the urease active site. Indole containing molecule 2 ($IC_{50}$=8.56±0.027 µM) also showed excellent activity, however, furan containing compounds such as 10 demonstrated an $IC_{50}$ value 17.83±0.07 µM. In other words the urease activity of Schiff bases of thiazoles seems to be depending upon azomethine and substituent on its carbon part and slight variation in substituent (in case of substituted phenyl group substituent on phenyl residue) affect the activity of compounds.

The kinetics studies of 10 most active compounds (1-10) have been performed, to fine out the mode of inhibitions of these compounds. These thiazoles derivatives inhibited the jack bean urease in a concentration-dependent manner with Ki values between 3.82-14.8 µM. These inhibitors are mixed and competitive-type inhibitors Table-2. Compounds 1, 3, 4, 6, 8 and 9 are mixed-type, while the compounds 2, 5, 7, and 10 are competitive inhibitors. In mixed-type of inhibition, both $K_m$ and $V_{max}$ are affected. The high $K_m$ and low $V_{max}$ of these compounds indicated a mixed-type of inhibition. In the presence of compounds 2, 5, 7, and 10, the $V_{max}$ of jack bean urease was not affected, while the $K_m$ increased which indicated a pure competitive-type of inhibition.

Three different methods were applied to determine the type of inhibition and Ki values for these inhibitors. Firstly by using Lineweaver-Burk plots the reciprocal of the rate of the reaction were plotted against the reciprocal of substrate concentration to monitor the effect of inhibitor on both $K_m$ and $V_{max}$. Secondly the secondary replots of Lineweaver-Burk plots were plotted to determine the Ki value. The Ki values were calculated by plotting the slope of each line in the Lineweaver-Burk plots against the different concentration of inhibitors. In third method the Ki values was confirmed from Dixon plot by plotting the reciprocal of the rate of reaction against the different concentration of inhibitors.

TABLE 2

The inhibition and kinetics parameters of urease by Schiff bases of thiazoles derivatives.

| Compounds | $IC_{50}$ (µM) | $K_m$ (mM) | $K_m$app (mM) | $V_{max}$ (µmol/min)$^{-1}$ | $V_{max}$app (µmol/min)$^{-1}$ | Ki (µM) ± S.E.M. | Type of Inhibition |
|---|---|---|---|---|---|---|---|
| 1 | 2.83 | 2.20 | 2.51 | 36 | 19.3 | 3.82 ± 0.004 | Mixed inhibition |
| 2 | 8.5 | 2.20 | 4.3 | 38.2 | 38.2 | 9.6 ± 0.0024 | Competitive inhibition |
| 3 | 7.9 | 2.25 | 3.87 | 23.36 | 15.80 | 9.7 ± 0.007 | Mixed inhibition |
| 4 | 11.16 | 2.25 | 2.56 | 23.47 | 12.85 | 9.23 ± 0.018 | Mixed inhibition |
| 5 | 7.6 | 2.25 | 5.09 | 21.64 | 23.5 | 13.6 ± 0.0123 | Competitive inhibition |

TABLE 2-continued

The inhibition and kinetics parameters of urease by Schiff bases of thiazoles derivatives.

| Compounds | $IC_{50}$ (μM) | $K_m$ (mM) | $K_m$app (mM) | $V_{max}$ (μmol/min)$^{-1}$ | $V_{max}$app (μmol/min)$^{-1}$ | $K_i$ (μM) ± S.E.M. | Type of Inhibition |
|---|---|---|---|---|---|---|---|
| 6 | 8.8 | 2.25 | 2.90 | 21.64 | 8.06 | 8.22 ± 0.0233 | Mixed inhibition |
| 7 | 9.33 | 2.25 | 6.28 | 28.8 | 29 | 11.89 ± 0.0040 | Competitive inhibition |
| 8 | 8.1 | 2.22 | 2.4 | 19.3 | 5.02 | 7.89 ± 0.0142 | Mixed inhibition |
| 9 | 14.5 | 2.2 | 3.22 | 19 | 8.72 | 12.39 ± 0.0168 | Mixed inhibition |
| 10 | 17.83 | 2.25 | 2.92 | 20.04 | 10.34 | 14.82 ± 0.0109 | Competitive inhibition |
| Standard (Thiourea) | 21 | 2.25 | 7.38 | 19.12 | 19.2 | 20.01 ± 0.020 | Competitive inhibition |

Result represents as mean of triplicate ± standard error of mean (S.E.M)

What is claimed is:

1. A method of treating kidney stones comprising administering to a mammal in need thereof an effective amount of a compound comprising:

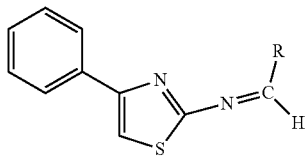

which is selected from the group consisting of
N-[5a,10c-Dihydro-1-pyrenylmethylidene]-N-(4-phenyl-1,3-thiazol-2-yl)amine;
N-[1H-indol-3-ylmethylidene]-N-(4-phenyl-1,3-thiazol-2-yl)amine;
2-Ethoxy-6-{[(4-phenyl-1,3-thiazol-2-yl)imino]methyl}phenol;
N-[4-Ethoxyphenyl)methylidene]-N-(4-phenyl-1,3-thiazol-2-yl)amine;
N-(4-Phenyl-1,3-thiazol-2-yl)-N-[4-pyridinylmethylidene]amine;
2-Methoxy-6-{[(4-phenyl-1,3-thiazol-2-yl)imino]methyl}phenol;
N-[2-Naphthylmethylidene]-N-(4-phenyl-1,3-thiazol-2-yl)amine;
4-Chloro-2-{[(4-phenyl-1,3-thiazol-2-yl)imino]methyl}phenol;
N-[4-Isopropylphenyl)methylidene]-N-(4-phenyl-1,3-thiazol-2-yl)amine;
N-[(5-Methyl-2-furyl)methylidene]-N-(4-phennyl-1,3-thiazol-2-yl)amine;
N-[4-Nitrophenyl)methylidene]-N-(4-phenyl-1,3-thiazol-2-yl)amine
4-{[4-Phenyl-1,3-thiazol-2-yl)imino]methyl}phenol;
N-[4-Methoxyphenyl)methylidene]-N-(4-phenyl-1,3-thiazol-2-yl)amine;
N-[4-(Dimethylamino)phenyl]methylidene}-N-(4-phenyl-1,3-thiazol-2-yl)amine;
N-(4-phenyl-1,3[Propylidene]amine;
2-{[(4-Phenyl-1,3-thiazol-2-yl)imino]methyl}phenol;
1-(2-Methoxyphenyl)-2-[(4-phenyl-1,3-thiazol-2-yl)imino]-1-ethanone;
N-[4-(Methylsulfanyl)phenyl]methylidene}-N-(4-phenyl-1,3-thiazol-2-yl)amine;
N-[Phenylmethylidene]-N-(4-phenyl-1,3-thiazol-2-yl)amine;
N-[2-Chlorophenyl)methylidene]-N-(4-phenyl-1,3-thiazol-2-yl)amine;
N-[1-Naphthylmethylidene]-N-(4-phenyl-1,3-thiazol-2-yl)amine;
N-[2-Fluorophenyl)methylidene]-N-(4-phenyl-1,3-thiazol-2-yl)amine;
3-{[(4-Phenyl-1,3-thiazol-2-yl)imino]methyl}-1,2-benzenediol;
N-[3,4-Dimethoxyphenyl)methylidene]-N-(4-phenyl-1,3-thiazol-2-yl)amine;
N-[2,6-Dichlorophenyl)methylidene]-N-(4-phenyl-1,3-thiazol-2-yl)amine;
N-[4-Chlorophenyl)methylidene]-N-(4-phenyl-1,3-thiazol-2-yl)amine;
4-Phenyl-N-[(2,3,4-trimethoxyphenyl)methylidene]-1,3-thiazol-2-amine; and
N-[3-Nitrophenyl)methylidene]-N-(4-phenyl-1,3-thiazol-2-yl)amine.

2. The method of claim 1, wherein the compound further comprises a pharmaceutically acceptable carrier or excipient.

3. The method of claim 1, wherein the mammal is a human.

* * * * *